US008920421B2

(12) United States Patent
Rupp

(10) Patent No.: US 8,920,421 B2
(45) Date of Patent: Dec. 30, 2014

(54) SYSTEM AND METHOD FOR TISSUE SEALING

(75) Inventor: Steven C. Rupp, Arvada, CO (US)

(73) Assignee: Covidien LP, Mansfield, MA (US)

( * ) Notice: Subject to any disclaimer, the term of this patent is extended or adjusted under 35 U.S.C. 154(b) by 1067 days.

(21) Appl. No.: 12/955,042

(22) Filed: Nov. 29, 2010

(65) Prior Publication Data

US 2012/0136354 A1  May 31, 2012

(51) Int. Cl.
*A61B 18/18* (2006.01)
*A61B 18/12* (2006.01)
*A61B 18/00* (2006.01)
*A61B 18/20* (2006.01)
*A61B 18/10* (2006.01)
*A61B 18/08* (2006.01)
*A61B 18/14* (2006.01)

(52) U.S. Cl.
CPC ...... *A61B 18/1206* (2013.01); *A61B 2018/1823* (2013.01); *A61B 2018/00875* (2013.01); *A61B 18/20* (2013.01); *A61B 18/10* (2013.01); *A61B 2018/00702* (2013.01); *A61B 2018/00648* (2013.01); *A61B 2018/0063* (2013.01); *A61B 18/085* (2013.01); *A61B 18/1445* (2013.01); *A61B 2018/00642* (2013.01); *A61B 18/1815* (2013.01)
USPC .......................................... 606/51

(58) Field of Classification Search
USPC .................................... 606/45–52
See application file for complete search history.

(56) References Cited

U.S. PATENT DOCUMENTS

| | | | |
|---|---|---|---|
| 6,312,391 | B1 | 11/2001 | Ramadhyani et al. |
| 6,562,037 | B2 | 5/2003 | Paton et al. |
| 6,989,010 | B2 | 1/2006 | Francischelli et al. |
| 7,025,764 | B2 | 4/2006 | Paton et al. |

(Continued)

FOREIGN PATENT DOCUMENTS

| | | |
|---|---|---|
| WO | WO 99/40857 | 8/1999 |
| WO | 01/74252 | 10/2001 |

(Continued)

OTHER PUBLICATIONS

European Search Report, Application No. EP 10 00 9732 dated Jan. 18, 2011.

(Continued)

*Primary Examiner* — Linda Dvorak
*Assistant Examiner* — Amanda Scott

(57) ABSTRACT

An electrosurgical system is disclosed. The system includes an electrosurgical forceps including first and second jaw members pivotally attached in opposing relation relative to one another, the jaw members relatively movable from a first, open position wherein the jaw members are disposed in spaced relation relative to one another to a second, clamping position wherein the jaw members cooperate to grasp tissue therebetween with a predetermined clamping force, each of the jaw members including an electrically conductive sealing surface. The system also includes an electrosurgical generator configured to operatively couple to the electrosurgical forceps and to supply electrosurgical energy to the electrically conductive sealing surfaces. The electrosurgical generator includes at least one input control configured to record a user-defined setting associated with the electrosurgical energy; at least one sensor configured to measure at least one tissue parameter or at least one electrosurgical energy parameter; and a controller configured to predict a tissue mass of the tissue grasped by the jaw members based on the at least one tissue parameter or at least one electrosurgical energy parameter and to adjust the user-defined setting as a function of the predicted tissue mass.

20 Claims, 6 Drawing Sheets

(56) References Cited

U.S. PATENT DOCUMENTS

| | | | |
|---|---|---|---|
| 7,137,980 B2 | 11/2006 | Buysse et al. | |
| 7,156,846 B2 | 1/2007 | Dycus et al. | |
| 7,258,688 B1 | 8/2007 | Shah | |
| 7,431,721 B2 | 10/2008 | Paton et al. | |
| 7,731,717 B2 | 6/2010 | Odom et al. | |
| 7,776,037 B2 | 8/2010 | Odom | |
| 7,901,400 B2 | 3/2011 | Wham et al. | |
| 2003/0229344 A1 | 12/2003 | Dycus et al. | |
| 2004/0010289 A1 | 1/2004 | Biggs et al. | |
| 2004/0254573 A1 | 12/2004 | Dycus et al. | |
| 2005/0004564 A1 | 1/2005 | Wham et al. | |
| 2005/0256522 A1 | 11/2005 | Francishelli et al. | |
| 2006/0259034 A1* | 11/2006 | Eder et al. | 606/50 |
| 2006/0259035 A1* | 11/2006 | Nezhat et al. | 606/50 |
| 2007/0282321 A1 | 12/2007 | Shah | |
| 2009/0157071 A1* | 6/2009 | Wham et al. | 606/33 |
| 2009/0157072 A1 | 6/2009 | Wham et al. | |
| 2009/0234353 A1 | 9/2009 | McPherson | |
| 2010/0016857 A1 | 1/2010 | McKenna et al. | |

FOREIGN PATENT DOCUMENTS

| | | |
|---|---|---|
| WO | 02/085229 | 10/2002 |
| WO | 2004/083797 | 9/2004 |
| WO | 2008/002517 | 1/2008 |
| WO | 2009/075879 | 6/2009 |

OTHER PUBLICATIONS

European Search Report for European Application No. 11190723.4 dated Mar. 8, 2012.

* cited by examiner

SYSTEM AND METHOD FOR TISSUE SEALING

BACKGROUND

1. Technical Field

The present disclosure relates to an electrosurgical system and method for performing electrosurgical procedures. More particularly, the present disclosure relates to sealing tissue, wherein one or more user-defined settings are adjusted automatically in response to the amount of the tissue mass detected by an electrosurgical instrument.

2. Background of Related Art

Electrosurgery involves application of high radio frequency electrical current to a surgical site to cut, ablate, or coagulate tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact of body tissue with either of the separated electrodes does not cause current to flow.

Bipolar electrosurgery generally involves the use of forceps. A forceps is a pliers-like instrument which relies on mechanical action between its jaws to grasp, clamp and constrict vessels or tissue. So-called "open forceps" are commonly used in open surgical procedures whereas "endoscopic forceps" or "laparoscopic forceps" are, as the name implies, used for less invasive endoscopic surgical procedures. Electrosurgical forceps (open or endoscopic) utilize mechanical clamping action and electrical energy to effect hemostasis on the clamped tissue. The forceps include electrosurgical conductive plates which apply the electrosurgical energy to the clamped tissue. By controlling the intensity, frequency and duration of the electrosurgical energy applied through the conductive plates to the tissue, the surgeon can coagulate, cauterize and/or seal tissue.

Tissue or vessel sealing is a process of liquefying the collagen, elastin and ground substances in the tissue so that they reform into a fused mass with significantly-reduced demarcation between the opposing tissue structures. Cauterization involves the use of heat to destroy tissue and coagulation is a process of desiccating tissue wherein the tissue cells are ruptured and dried.

Tissue sealing procedures involve more than simply cauterizing or coagulating tissue to create an effective seal; the procedures involve precise control of a variety of factors. For example, in order to affect a proper seal in vessels or tissue, it has been determined that two predominant mechanical parameters must be accurately controlled: the pressure applied to the tissue; and the gap distance between the electrodes (i.e., distance between opposing jaw members or opposing sealing surfaces). In addition, electrosurgical energy must be applied to the tissue under controlled conditions to ensure creation of an effective vessel seal.

SUMMARY

According to one embodiment of the present disclosure, an electrosurgical system is disclosed. The system includes an electrosurgical forceps including first and second jaw members pivotally attached in opposing relation relative to one another, the jaw members relatively movable from a first, open position wherein the jaw members are disposed in spaced relation relative to one another to a second, clamping position wherein the jaw members cooperate to grasp tissue therebetween with a predetermined clamping force, each of the jaw members including an electrically conductive sealing surface. The system also includes an electrosurgical generator configured to operatively couple to the electrosurgical forceps and to supply electrosurgical energy to the electrically conductive sealing surfaces. The electrosurgical generator includes at least one input control configured to record a user-defined setting associated with the electrosurgical energy; at least one sensor configured to measure at least one tissue parameter or at least one electrosurgical energy parameter; and a controller configured to predict a tissue mass of the tissue grasped by the jaw members based on the at least one tissue parameter or at least one electrosurgical energy parameter and to adjust the user-defined setting as a function of the predicted tissue mass.

According to another embodiment of the present disclosure, an electrosurgical system is disclosed. The system includes an electrosurgical forceps including first and second jaw members pivotally attached in opposing relation relative to one another, the jaw members relatively movable from a first, open position wherein the jaw members are disposed in spaced relation relative to one another to a second, clamping position wherein the jaw members cooperate to grasp tissue therebetween with a predetermined clamping force, each of the jaw members including an electrically conductive sealing surface. The system also includes an electrosurgical generator configured to operatively couple to the electrosurgical forceps and to supply electrosurgical energy to the electrically conductive sealing surfaces. The electrosurgical generator includes at least one input control configured to record a user-defined setting associated with the electrosurgical energy; at least one sensor configured to measure at least one electrosurgical energy parameter suitable for determining total energy delivered to tissue; and a controller configured to predict a tissue mass of the tissue grasped by the jaw members based on the total energy delivered to tissue prior to application of therapeutic energy to the tissue and to adjust the user-defined setting as a function of the predicted tissue mass.

A method for performing an electrosurgical procedure is also contemplated by the present disclosure. The method includes grasping tissue with an electrosurgical forceps, the electrosurgical forceps adapted to connect to an electrosurgical energy source configured to supply electrosurgical energy thereto, the electrosurgical forceps including first and second jaw members pivotally attached in opposing relation relative to one another, the jaw members relatively movable from a first, open position wherein the jaw members are disposed in spaced relation relative to one another to a second, clamping position wherein the jaw members cooperate to grasp tissue therebetween with a predetermined clamping force, each of the jaw members including an electrically conductive sealing surface. The method also includes recording a user-defined setting associated with the electrosurgical energy; supplying the electrosurgical energy to the electrically conductive sealing surfaces; measuring at least one tissue parameter or at least one electrosurgical energy parameter; predicting a tissue mass of the tissue grasped by the jaw members based on the at least one tissue parameter or at least one electrosurgical energy parameter; and adjusting the user-defined setting as a function of the predicted tissue mass.

BRIEF DESCRIPTION OF THE DRAWINGS

Various embodiments of the present disclosure are described herein with reference to the drawings wherein.

DETAILED DESCRIPTION

Figure 1:
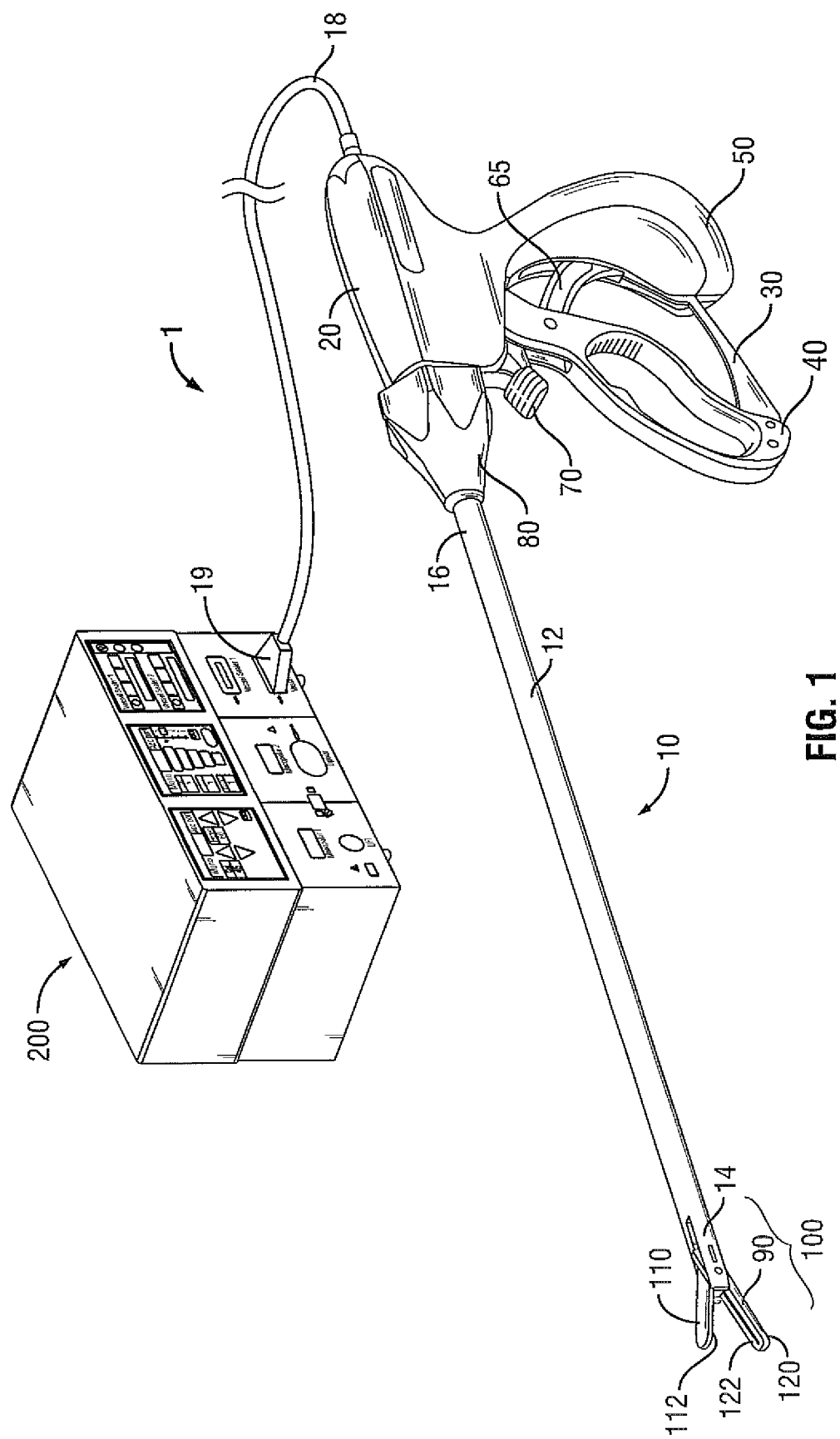
FIG. 1 is a schematic block diagram of an electrosurgical system according to one embodiment of the present disclosure.

Particular embodiments of the present disclosure will be described hereinbelow with reference to the accompanying drawings. In the following description, well-known functions or constructions are not described in detail to avoid obscuring the present disclosure in unnecessary detail. Those skilled in the art will understand that the present disclosure may be adapted for use with either an endoscopic instrument or an open instrument. It should also be appreciated that different electrical and mechanical connections and other considerations may apply to each particular type of instrument, however, the novel aspects with respect to vessel and tissue sealing are generally consistent with respect to both the open or endoscopic designs.

In the drawings and in the description which follows, the term "proximal", refers to the end of the electrosurgical forceps 10 which is closer to the user, while the term "distal" refers to the end of the forceps which is further from the user.

FIG. 1 is a schematic illustration of an electrosurgical system 1. The system 1 includes an electrosurgical forceps 10 for treating patient tissue. Electrosurgical RF energy is supplied to the forceps 10 by a generator 200 via a cable 18 thus allowing the user to selectively coagulate and/or seal tissue.

As shown in FIG. 1, the forceps 10 is shown as an endoscopic version of a vessel sealing bipolar forceps. In embodiments, the forceps 10 may be any suitable electrosurgical sealing instrument, such as open-type forceps. The forceps 10 is configured to support an effector assembly 100 and generally includes a housing 20, a handle assembly 30, a rotating assembly 80, and a trigger assembly 70 which mutually cooperate with the end effector assembly 100 to grasp, seal and, if required, divide tissue. Forceps 10 also includes a shaft 12 having a distal end 14 that mechanically engages the end effector assembly 100 and a proximal end 16 that mechanically engages the housing 20 proximate the rotating assembly 80.

The forceps 10 also includes a plug 19 that connects the forceps 10 to a source of electrosurgical energy, e.g., generator 200, via cable 18. Handle assembly 30 includes a fixed handle 50 and a movable handle 40. Handle 40 moves relative to the fixed handle 50 to actuate the end effector assembly 100 and enable a user to selectively grasp and manipulate tissue.

Figure 2:
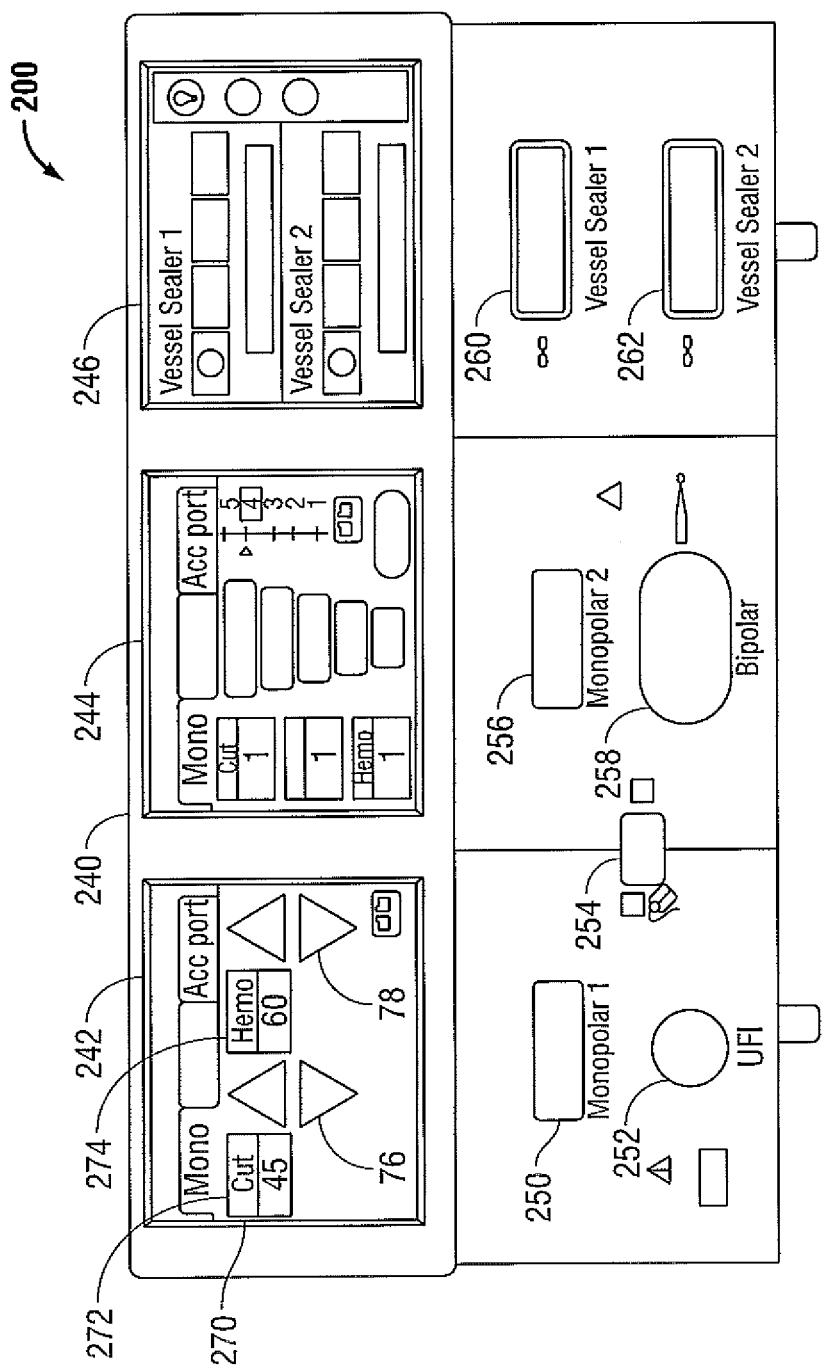
FIG. 2 is a front view of an electrosurgical generator according to an embodiment of the present disclosure.
Figure 3:
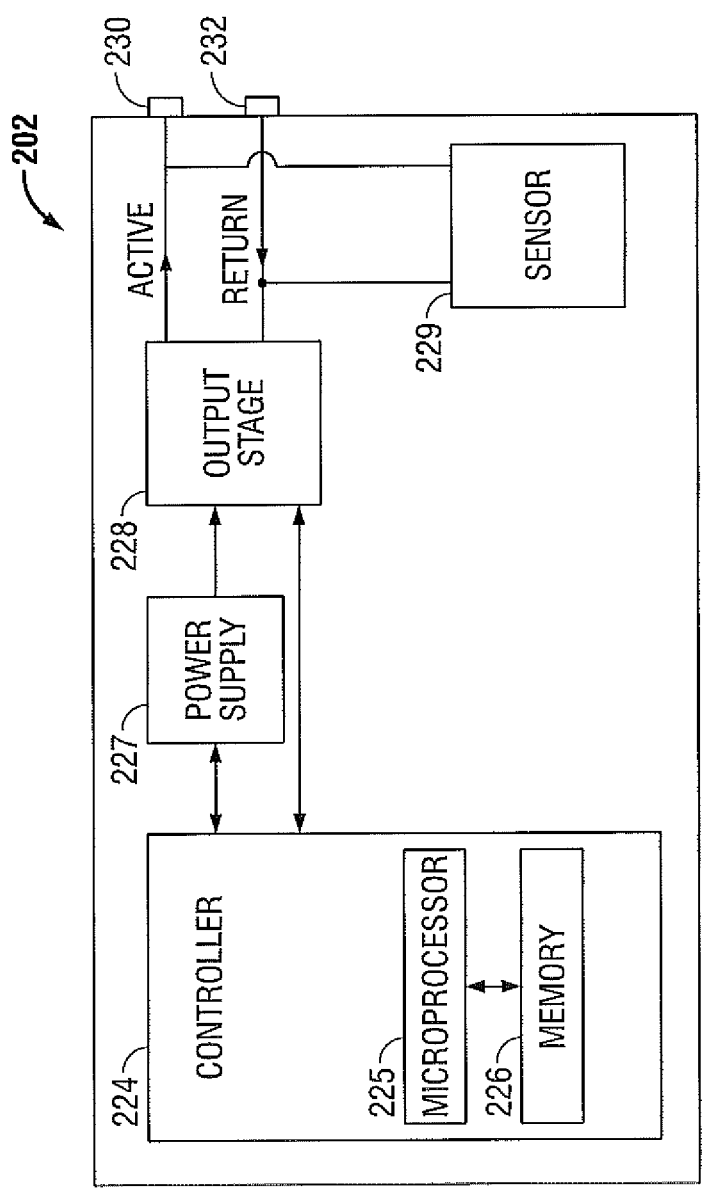
FIG. 3 is a schematic block diagram of the electrosurgical generator of FIG. 2 according to an embodiment of the present disclosure.

The end effector assembly 100 includes a pair of opposing jaw members 110 and 120 each having an electrically conductive sealing surfaces 112 and 122, respectively, attached thereto for conducting electrosurgical energy through tissue held therebetween. With reference to FIGS. 1-3, the electrically conductive sealing surfaces 112 and 122 are connected to the generator 200 through cable 18 that includes the supply and return leads coupled to the active and return terminals 230, 232 (FIG. 3), respectively. The electrosurgical forceps 10 is coupled to the generator 200 via the plug 19 at a connector 260 or 262 (FIG. 2), each of which is coupled to the active and return terminals 230 and 232 (e.g., pins, etc.).

The jaw members 110 and 120 move in response to movement of handle 40 from an open position to a closed position. In the open position, the sealing surfaces 112 and 122 are disposed in spaced relation relative to one another. In a clamping or closed position, the sealing surfaces 112 and 122 cooperate to grasp tissue and apply electrosurgical energy thereto. Jaw members 110 and 120 are activated using a drive assembly (not shown) enclosed within the housing 20. The drive assembly cooperates with the movable handle 40 to impart movement of the jaw members 110 and 120 from the open position to the clamping or closed position. Examples of a handle assemblies are shown and described in commonly-owned U.S. application Ser. No. 10/369,894 entitled "VESSEL SEALER AND DIVIDER AND METHOD MANUFACTURING SAME" and commonly owned U.S. application Ser. No. 10/460,926 entitled "VESSEL SEALER AND DIVIDER FOR USE WITH SMALL TROCARS AND CANNULAS" which are both hereby incorporated by reference herein in their entirety.

With reference to FIG. 2, front face 240 of the generator 200 is shown. The generator 200 may be any suitable type (e.g., electrosurgical, microwave, etc.) and may include a plurality of connectors 250-262 to accommodate various types of electrosurgical instruments (e.g., electrosurgical forceps 10, etc.). The connectors 250-262 may include various detection devices that can read identifying information encoded on the plug 19 of the forceps 10. The connectors 250-262 are configured to decode the information encoded on the plug 19 that corresponds to the operating parameters of the instrument, such as jaw fill, jaw size, etc. allowing the generator 200 to preset energy delivery settings based on the connected instrument. In embodiments, data may be encoded in bar codes, electrical components (e.g., resistors, capacitors, etc.), RFID chips, magnets, non-volatile memory, etc., which may then be coupled to or integrates into the plug 19. Corresponding detection devices may include, but are not limited to, bar code readers, electrical sensors, RFID readers, Hall Effect sensors, memory readers, etc. and any other suitable decoders configured to decode data encoded on the plug 19.

The generator 200 includes one or more display screens 242, 244, 246 for providing the user with variety of output information (e.g., intensity settings, treatment complete indicators, etc.). Each of the screens 242, 244, 246 is associated with corresponding connector 250-262. The generator 200 includes suitable input controls (e.g., buttons, activators, switches, touch screen, etc.) for controlling the generator 200. The display screens 242, 244, 246 are also configured as touch screens that display a corresponding menu for the electrosurgical instruments (e.g., electrosurgical forceps 10, etc.). The user then makes inputs by simply touching corresponding menu options.

The screen 242 controls monopolar output and the devices connected to the connectors 250 and 252. The connector 250 is configured to couple to monopolar electrosurgical instrument (e.g., electrosurgical pencil) and the connector 252 is configured to couple to a foot switch (not shown). The foot switch provides for additional inputs (e.g., replicating inputs of the generator 200). The screen 244 controls monopolar and bipolar output and the devices connected to the connectors 256 and 258. Connector 256 is configured to couple to other monopolar instruments. Connector 258 is configured to couple to a bipolar instrument (not shown).

Figure 6:
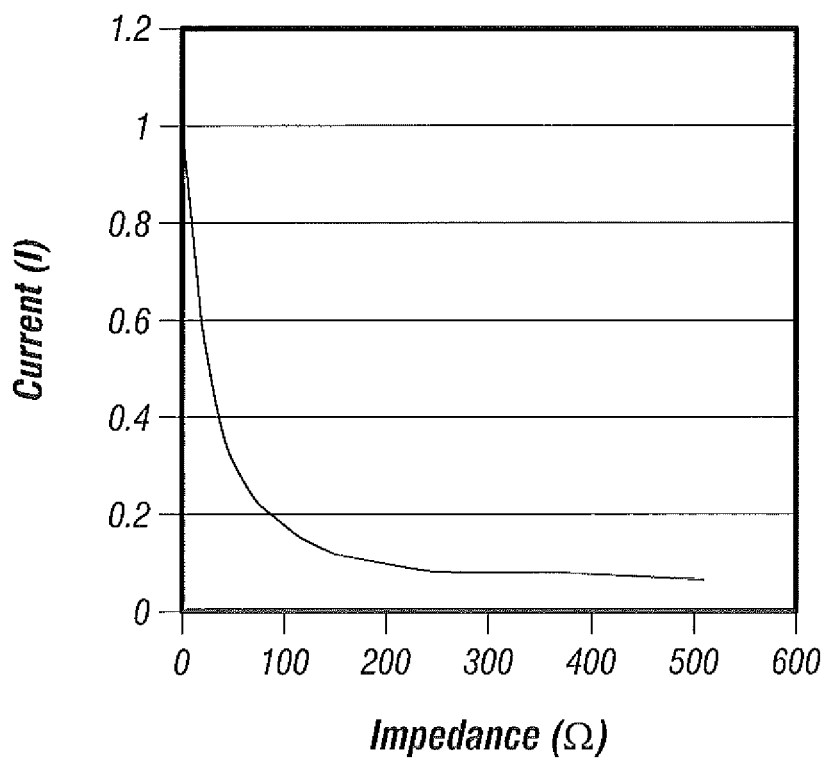
FIG. 6 shows a current versus impedance control curve according to the present disclosure.

The screen 246 controls bipolar sealing procedures performed by the forceps 10 that may be plugged into the connectors 260 and 262. The generator 200 outputs energy through the connectors 260 and 262 suitable for sealing tissue grasped by the forceps 10. In particular, the screen 246 outputs a user interface that allows the user to input a user-defined intensity setting. The user-defined setting may be any setting that allows the user to adjust one or more energy delivery parameters, such as power, current, voltage, energy, etc. or sealing parameters, such as pressure, sealing duration, etc. The user-defined setting is transmitted to the controller 224 where the setting may be saved in memory 226. In embodiments, the intensity setting may be a number scale, such as from one to ten or one to five. In embodiments, the intensity setting may be associated with a current curve of the generator 200 as shown in FIG. 6 and discussed in more detail below. The intensity settings may be specific for each forceps 10 being utilized, such that various instruments provide the user with a specific intensity scale corresponding to the forceps 10.

FIG. 3 shows a schematic block diagram of the generator 200 configured to output electrosurgical energy. In another embodiment, the generator 200 may be configured to output other types of energy such as, microwave, laser, etc. to power various other tissue treatment devices, such as microwave antennas, ultrasonic forceps, lasers, resistive heating electrodes, etc. The generator 200 includes a controller 224, a power supply 227 ("HVPS"), which may be a high voltage DC power supply, and an output stage 228. The HVPS 227 is connected to an AC source (e.g., electrical wall outlet) and provides high voltage DC power to an output stage 228, which then converts high voltage DC power into treatment energy (e.g., laser, ultrasonic, electrosurgical or microwave) and delivers the energy to the active terminal 230. The energy is returned thereto via the return terminal 232. The output stage 228 is configured to operate in a plurality of modes, during which the generator 200 outputs corresponding waveforms having specific duty cycles, peak voltages, crest factors, etc. In another embodiment, the generator 200 may be based on other types of suitable power supply topologies.

The controller 224 includes a microprocessor 225 operably connected to a memory 226, which may be volatile type memory (e.g., RAM) and/or non-volatile type memory (e.g., flash media, disk media, etc.). The microprocessor 225 includes one or more output ports that are connected to the HVPS 227 and/or output stage 228 allowing the microprocessor 225 to control the output of the generator 200 according to either open and/or closed control loop schemes. Those skilled in the art will appreciate that the microprocessor 225 may be substituted by any logic processor (e.g., control circuit) adapted to perform the calculations discussed herein.

The generator 200 also includes a plurality of sensors 229 to measure a variety of tissue and energy properties (e.g., tissue impedance, tissue temperature, output power, current and/or voltage, etc.), and provide feedback to the controller 224. Such sensors are within the purview of those skilled in the art. The controller 224 then signals the HVPS 227 and/or output stage 228, which then adjusts the DC and/or power supply, respectively. The controller 224 also receives input signals from the input controls of the generator 200 or the forceps 10, as discussed above. The controller 224 utilizes the input signals to adjust power outputted by the generator 200 and/or performs other control functions thereon.

It is known that sealing of the tissue is accomplished by virtue of a unique combination of gap control, pressure and electrical control. In other words, controlling the intensity, frequency and duration of the electrosurgical energy applied to the tissue through the sealing surface 112 and 122 are important electrical considerations for sealing tissue. In addition, two mechanical factors play an important role in determining the resulting thickness of the sealed tissue and the effectiveness of the seal, i.e., the pressure applied between the opposing jaw members 110 and 120 (between about 3 kg/cm2 to about 16 kg/cm2) and the gap distance between the opposing sealing surfaces 112 and 122 of the jaw members 110 and 120, respectively, during the sealing process (between about 0.001 inches to 0.006 inches). One or more stop members may be employed on one or both sealing surfaces to control the gap distance. A third mechanical factor has recently been determined to contribute to the quality and consistency of a tissue seal, namely the closure rate of the electrically conductive surfaces or sealing surfaces during activation.

The system 1 according to present disclosure regulates application of energy and pressure to achieve an effective seal capable of withstanding high burst pressures. The generator 200 applies energy to tissue at constant current based on the current control curve of FIG. 6 which is discussed in more detail below. Energy application is regulated by the controller 224 pursuant to an algorithm stored within the memory 226. In embodiments, the algorithm may apply energy to the tissue at constant voltage. The algorithm varies output based on the type of tissue being sealed. For instance, thicker tissue typically requires more power, whereas thinner tissue requires less power. Therefore, the algorithm adjusts the output based on tissue type by modifying specific variables (e.g., voltage being maintained, duration of power application etc.).

Figure 4A:
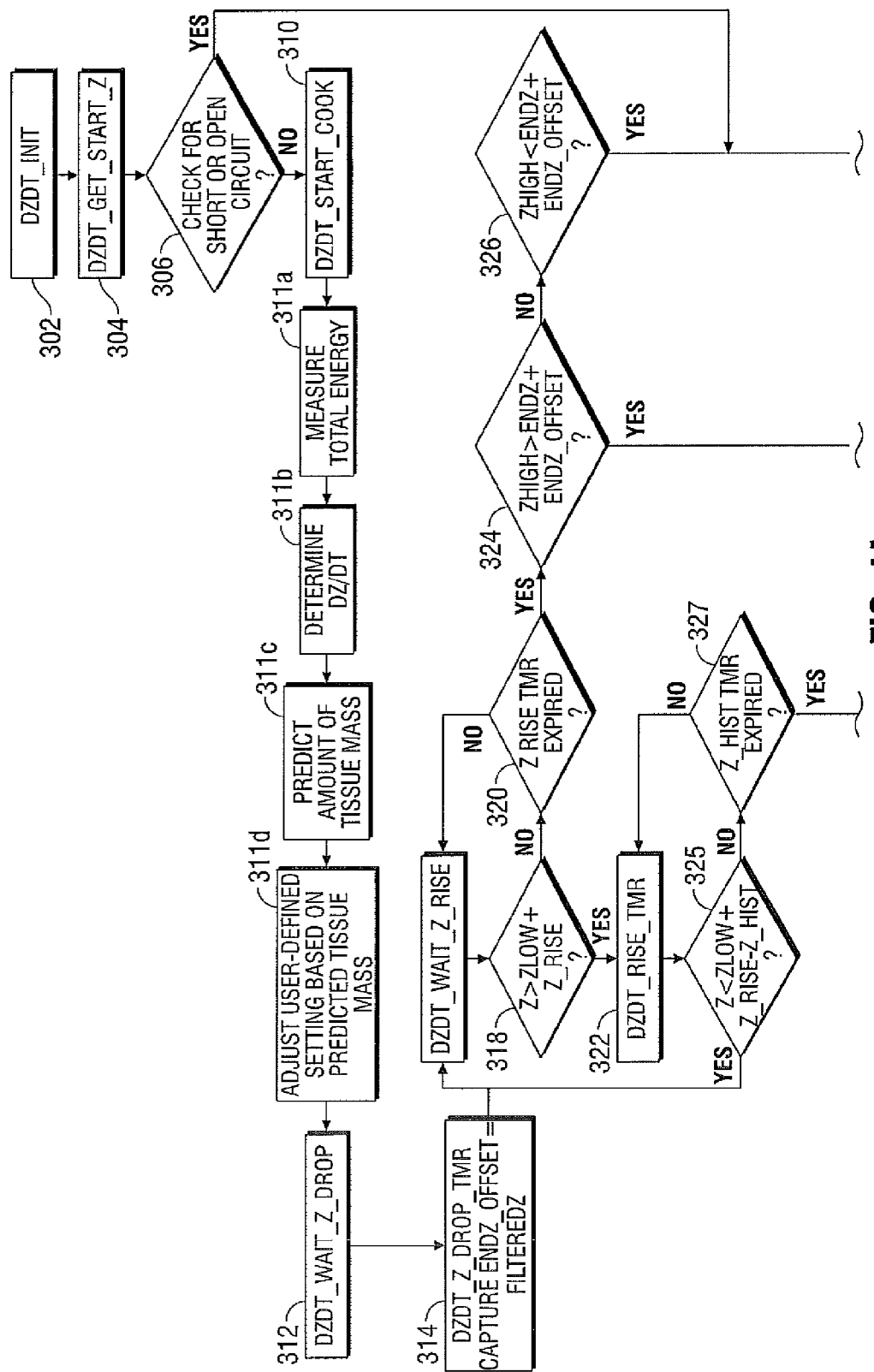
FIGS. 4A-B shows a flow chart showing a sealing method according to the present disclosure.
Figure 4B:
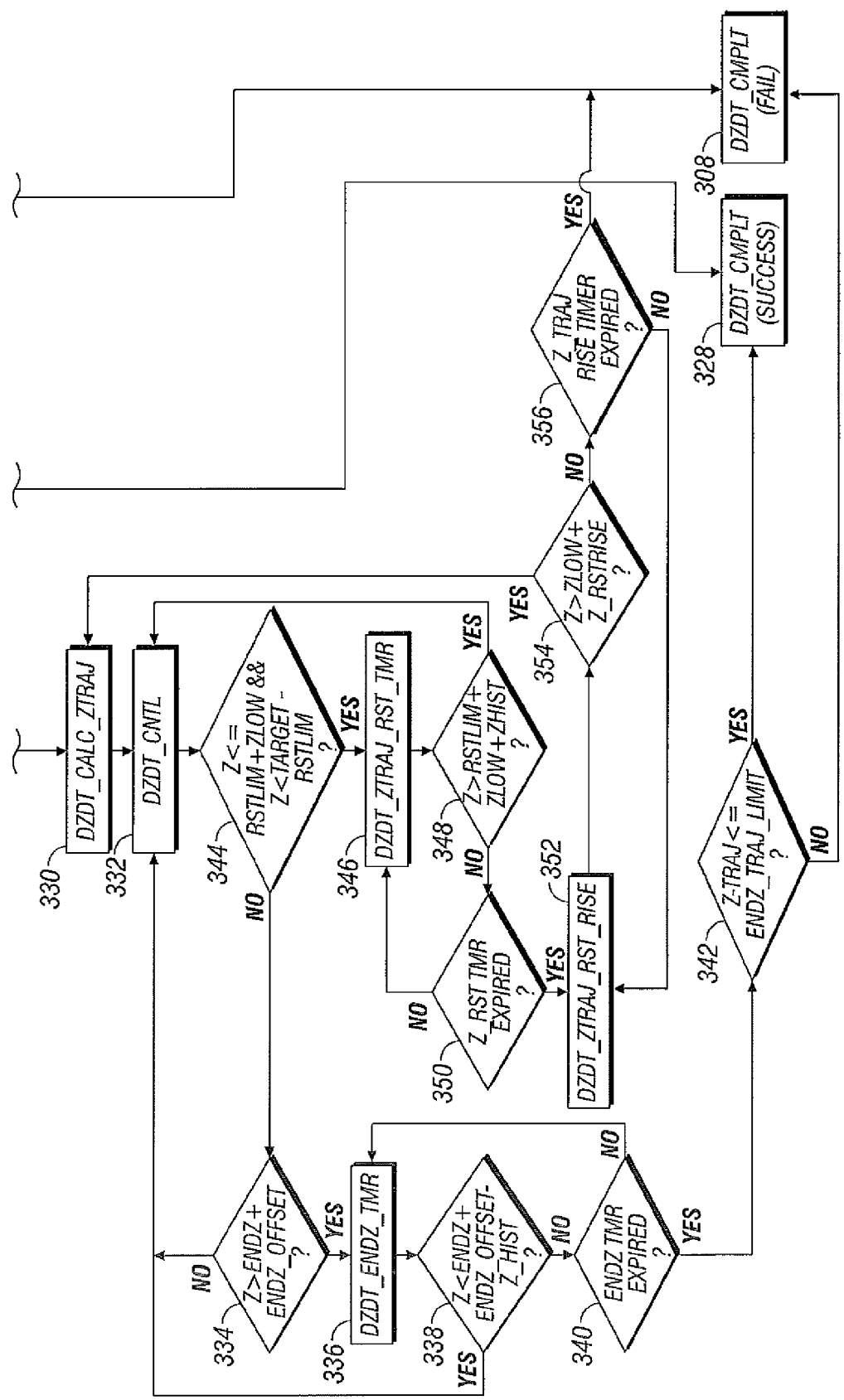
Figure 5:
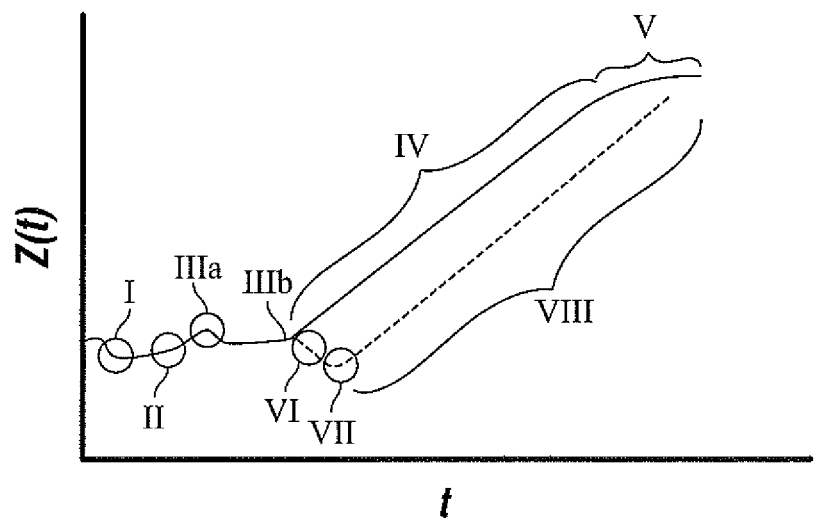
FIG. 5 shows a graph illustrating the changes occurring in tissue impedance during sealing utilizing the method shown in FIGS. 4A-B.

The method of sealing tissue according to the present disclosure is discussed below with reference to FIGS. 4A-B. In addition, FIG. 5 shows a graph illustrating the changes to tissue impedance when tissue is sealed utilizing the method of FIGS. 4A-B. The method is embodied in a software-based algorithm which is stored in memory 226 and is executed by microprocessor 225.

In step 302, the vessel sealing procedure is activated (e.g., by pressing of a foot pedal or handswitch) and a host processor (e.g., microprocessor 225) activates a vessel sealing algorithm and loads a configuration file. The configuration file includes a variety of variables which control the algorithm (e.g., EndZ). Certain variables of the configuration file are adjusted based on the instrument being used and the bar settings selected by surgeon.

In step 304, the algorithm begins with an impedance sense phase, shown as phase I in FIG. 5, during which the algorithm senses the tissue impedance with an interrogatory impedance sensing pulse of from about 10 milliseconds (ms) to about 100 ms. Tissue impedance is determined without appreciably changing the tissue. During this interrogation or error-checking phase the generator 200 provides constant power to check for a short or an open circuit, in order to determine if tissue is being grasped.

In step 306, a determination is made whether the measured impedance is greater than a pre-programmed high impedance threshold, represented by the variable ImpSense_HiLimit, or less than a pre-programmed low impedance threshold, represented by the variable ImpSense_LowLimit. If in step 306 a short circuit is detected, e.g., impedance is below the low impedance threshold, in step 308, the algorithm exits with a regrasp alarm, otherwise, the algorithm starts the cook phase in step 310. The generator 200 then generates the pre-programmed ramping of current in its outer-loop and constant current per current curve within its inner-loop according to the current control curve shown in FIG. 6.

The curve of FIG. 6 may be modified by intensity settings input into the generator via the display 246. In particular, selecting a specific intensity setting (e.g., low, medium, high, etc.) selects a corresponding value, represented by a variable, Cook_AmpMult, which then multiplies the curve. The Cook_AmpMult variable is specified in the configuration file and may be from about 2 Amps to about 5.5 Amps.

The control curve of FIG. 6 is shown as a current curve which decreases rapidly from low impedances to high, although it could also be represented as a power or voltage curve. The control curve is configured to reduce power with increasing impedances higher than about 24 ohms. This shape provides several advantages: 1) this curve provides for high power delivery with low impedance tissues, which allows the tissue to heat rapidly at the start of the seal cycle; 2) this shape tames the positive feedback caused by an increase in delivered power as a result of increasing impedance; 3) the curve allows a slower control system for impedance control since the output power is reduced as the impedance rises, thus keeping the tissue impedance from rising too quickly.

After the error checking phase, in step 310, the algorithm initiates a first application of the RF energy by delivering current linearly over time to heat the tissue. RF energy may be delivered in a non-linear or in a time-independent step manner from zero to an "on" state. Delivery may be controlled through other parameters such as voltage, current, power and/or energy. Once initiated, the ramping of energy continues until one of two events occurs: 1) the maximum allowable value is reached or 2) the tissue "reacts." The term "tissue reaction" is a point at which intracellular and/or extra-cellular fluid begins to boil and/or vaporize, resulting in an increase in tissue impedance. In the case when the maximum allowable value is reached, the maximum value is maintained until the tissue "reacts." In the event that the tissue reacts prior to reaching the maximum value, the energy required to initiate a tissue "reaction" has been attained and the algorithm moves to an impedance control state.

Tissue reaction may be identified by two factors. The first factor is identified based on the minimum tissue impedance obtained during the heating period. In step 312, the algorithm continuously monitors the tissue impedance after the onset of energy to identify the lowest value reached and then in step 314 stores this value as the variable ZLow. As time progresses throughout the entire energy activation cycle, the stored value is updated anytime a new value is read that is lower than the previous Zlow, represented by phase II in FIG. 5. In other words, during steps 312, 314 and 316, the generator 200 waits for the tissue impedance to drop. The generator 200 also measures and records offset impedance as a variable, EndZ_Offset, which corresponds to the initial measured tissue impedance. The EndZ_Offset impedance is used to determine the threshold for terminating the procedure. In step 314, EndZ_Offset impedance is measured at the start of the procedures, specifically at about 100 ms after initial application of electrosurgical energy, which occurs approximately during phase I.

The second factor in identifying tissue reaction is based on a predetermined rise in impedance. This is represented by the variable Z_Rise, which is loaded from the configuration file and may be from about 1Ω to about 750Ω. In step 316 the algorithm waits for a predetermined period of time to identify whether a rise in impedance has occurred, represented by phases IIIa and IIIb in FIG. 5. In step 318, the algorithm repeatedly attempts to identify a tissue reaction by determining if $Z(t) > ZLow + Z\_Rise$ where $Z(t)$ is the impedance at any time during sampling. In step 320, the algorithm verifies whether the timer for waiting for the impedance to rise has expired.

If the tissue does not rise within the predetermined period of time (e.g., in step 320 the timer has expired) then, the generator 200 issues a regrasp due to the tissue not responding. In particular, in step 324 the generator 200 verifies whether the procedure is complete by comparing measured impedance to the impedance threshold. If the measured impedance is greater than the impedance threshold, the algorithm proceeds to step 328 and the seal process is complete. This step prevents sealing tissue that has already been sealed. If the tissue is not sealed, then in step 326 the generator determines whether the measured impedance is below the impedance threshold, and, if so, then the generator 200 issues a regrasp alarm in step 308.

To check for the reaction stability, the algorithm has a hysteresis identifier stored as a variable, Z_HIST, defined by a specified drop in impedance occurring in under a specified duration in time. This is used to filter out the noise which may be mistaken by the algorithm for the actual rise in impedance. In step 325, the algorithm determines whether the measured impedance is less than the rise in impedance above the lowest impedance minus the hysteresis identifier (i.e., $Z(t) < Zlow + Z\_Rise - Z\_Hist$). Step 325 is repeated for a specified period of time, which is stored as a variable Z_Hist tmr, by determining whether a timer has expired in step 322, the repetition of the loop is determined in step 327.

During tissue reaction phase, namely phases I, II, IIIa, and IIIb, prior to application of therapeutic energy to the tissue, the generator 200 is also configured to predict the amount of tissue mass being held between the electrically conductive sealing surfaces 112 and 122. In embodiments, the generator 200 determines the total amount of energy supplied to the tissue that is needed to achieve tissue reaction and based on the energy measurements predicts the amount of tissue mass held between the jaw members 110 and 120. In further embodiments, the generator 200 determines the rate of change of the impedance during energy application to achieve tissue reaction and based on the rate of change of impedance predicts the tissue mass. The generator 200 then adjusts predefined user settings, such as intensity settings, based on the predicted tissue mass. In embodiments, the generator 200 increases the intensity settings if the predicted tissue mass is above a predetermined threshold and lowers the intensity settings if the tissue mass is below. The generator 200 may also include other mechanisms for determining tissue mass, such as by measuring the pressure applied by the jaw members 110 and 120, the gap distance therebetween and the opacity of tissue.

In step 311*a*, the generator 200 measures the total amount of energy being supplied to the tissue during the determination of tissue reaction. The generator 200 may determine total energy by measuring voltage and current and determining average power supplied to the tissue during the tissue reaction time.

In step 311*b*, the generator 200 determines the rate of change of impedance (dZ/dt) by measuring impedance at a plurality of instances and obtaining the derivative of the collection of impedance versus time values. In embodiments, the microprocessor 225 (FIG. 3) continuously acquires a current impedance value Zn and stores the value along with a time instance associated therewith in the memory 226. The value of "n" is incremented and compared with a predefined value to determine whether a sufficient number of impedances have been measured, in order to calculate dZ/dt. For example, dZ/dt may be calculated by taking the measured impedance Zn and comparing it to the preceding measured impedance Zn-1, in which case n would have to be greater or equal to 2 in order for dZ/dt to be calculated. Alternatively, dZ/dt may be calculated by taking the measured impedance Zn and comparing it to the previously measured impedance Zn-2, in which case n would have to be greater or equal to 3 in order for dZ/dt to be calculated. If "n" is less than the minimum number of impedance values, the microprocessor 225 waits for an impedance sampling interval which may be, for example, about 0.2 seconds, and then triggers an impedance measurement again. This process continues until there are a sufficient number of collected impedance measurements to calculate dZ/dt, at which point the microprocessor 225 employs the stored impedance measurements to calculate dZ/dt, which in embodiments, may be calculated using the following formula: $(1/(2\Delta t1))*(Zn-Zn-2)$.

In step 311c, the calculated total energy and/or dZ/dt are used to determine the amount of tissue mass. In embodiments, a look-up table may be stored in the memory 226, which includes a plurality of tissue mass values associated with specific energy and dZ/dt values. In embodiments, the memory 226 may store a plurality of tissue mass look-up tables, each of which is loaded when a corresponding forceps 10 is being utilized. The generator 200 may load a corresponding look-up table upon reading the plug 19, as discussed above. The generator 200 then obtains the predicted tissue mass value based on the calculated total energy and/or dZ/dt from the look-up table.

In step 311d, the generator 200 compares the predicted tissue mass value to a predetermined or expected tissue mass threshold. If the predicted tissue mass value differs from the expected tissue mass threshold by a set amount, in embodiments from about 5% to about 50%, in embodiments from about 10% to about 25%, the generator 200 adjusts the user-defined settings, namely the intensity settings accordingly.

In embodiments, the settings may be adjusted as a function of the offset of the predicted tissue mass from the expected tissue mass. In embodiments, the adjustment may be proportional, logarithmic, exponential, etc. If the intensity settings are based on a scale as discussed above, the generator 200 automatically adjusts the user-defined settings, by either lowering or increasing the setting in response to the difference between predicted and expected tissue mass. The intensity setting is then utilized to adjust the current curve and other energy output settings of the generator 200 throughout the duration of the procedure.

After the tissue reacts and tissue impedance begins to rise, if the impedance drops below a hysteresis value within an allotted time, the system identifies the event as "not stable" as shown in phase IIIa. The algorithm also begins looking for the next rise in impedance by determining if the measured impedance is greater than the specified level of impedance, defined by the following formula: $Z(t)<Zlow+Z\_Rise-Z\_Hist$. If the timer expires and the impedance has not dropped below the hysteresis value, the reaction is considered stable and the impedance control state is implemented.

Once it is established that the tissue has reacted as shown in phase IIIb, the algorithm calculates the desired impedance trajectory based on the actual impedance and the desired rate of change of impedance in step 330. In step 332, the algorithm calculates a target impedance value for the control system at each time-step, based on a predefined desired rate of change of impedance (dZ/dt), represented as phase IV in FIG. 5. The desired rate of change may be stored as a variable and be loaded during the step 302. The control system then attempts to adjust the tissue impedance to match the target impedance. The target impedance takes the form of a target trajectory with the initial impedance value and time taken when the tissue reaction is considered real and stable. The trajectory may take a non-linear and/or quasi-linear form. Thus, when the measured impedance is greater than the rise in impedance above lowest impedance (i.e., $Z(t)>ZLow+ZRise$), the algorithm calculates a Z trajectory based on the actual impedance and desired dZ/dt, selected manually or automatically based on tissue type determined by the selected instrument.

The target impedance trajectory includes a plurality of a target impedance values at each time step. The algorithm drives tissue impedance along the target impedance trajectory by adjusting power output level to substantially match tissue impedance to a corresponding target impedance value. While the algorithm continues to direct the RF energy to drive the tissue impedance to match the specified trajectory, the algorithm monitors the impedance to make the appropriate corrections. The algorithm determines whether tissue fusion is complete and the system should cease RE energy in phase V as shown in FIG. 5. This is determined by monitoring the actual measured impedance rising above a predetermined threshold and staying above the threshold for a predetermined period of time. The threshold is defined as a specified level, EndZ, above the initial impedance value, EndZ_Offset. This determination minimizes the likelihood of terminating electrosurgical energy early when the tissue is not properly or completely sealed.

In step 334, it is determined if the measured impedance is greater than the specified level of impedance above the initial impedance value (i.e., $Z(t)>EndZ+EndZ\_Offset$) and, if yes, the algorithm verifies whether this state is maintained for the given time. In step 336, the algorithm initializes the timer, DZDT_ENDZ_TIMER. In step 338, the algorithm performs the determination of step 334 for the duration of the timer DZDT_ENDZ_TIMER, which may be about 400 ms, the expiration of which is verified in step 340. If the entire sealing processes has exceeded a predetermined time period (e.g., maximum seal timer) which may be about 12 seconds, the algorithm exits with an alarm. This alerts the user to a possible unfused tissue condition.

In embodiments, the EndZ value may be from about 10 ohms to about 1000 ohms above the minimum impedance reached and EndZ_Offset may be tissue impedance measured approximately about 100 ms after the onset of RF energy. Furthermore, the time duration for a cycle shut-off condition to verify tissue fusion has occurred, (i.e., the value of DZDT_ENDZ_TIMER) may be from about 0 seconds to about 2 seconds. The value of the EndZ_Offset could be calculated from a variety of different methods and utilizing a variety of different parameters such as the starting tissue impedance, the minimum impedance, the impedance at maximum current or minimum voltage, the impedance at either a positive or negative slope change of impedance, and/or a constant value specified within the programming or by the end user.

Once the timer expires and if the measured impedance is still above EndZ+EndZ_Offset the RF is shut off. However, it must be verified whether tissue reaction has not occurred too quickly (e.g., the control system failed to maintain control). This event is identified if the final measured impedance value deviated from the end target value by greater than a predetermined value, ENDZ_TRAJ_LIMIT. The ENDZ_TRAJ_LIMIT may be from about 1 ohm to about 500 ohms. In step 342, the algorithm determines whether the measured impedance is below ENDZ_TRAJ_LIMIT, and, if so, then in step 328 the algorithm issues a seal complete signal (e.g., audio and/or visual indication). This event aids in mitigating the occurrences of the algorithm terminating while the tissue is not fused.

Prior to proceeding to step 334 to determine if the seal process is complete, the algorithm performs a plurality of error checks. In particular, the algorithm determines whether excessive fluid has entered the field or an object has been encountered that causes the impedance to drop unexpectedly to affect the ongoing tissue reaction. This event is identified by a negative deviation between the target impedance and tissue impedance (e.g., tissue impedance is less than target impedance) as represented by phase VI in FIG. 5. Therefore, to identify that this event has occurred and is real (e.g. not an arcing event) several conditions are verified. In step 344, the algorithm determines whether the impedance dropped below a reset threshold value, RstLim, above the lowest impedance reached, ZLow and whether the impedance deviated sufficiently from the target request. This event is calculated based on the following formula: $Z(t) <= RstLim + ZLow$ & $Z(t) < target - RstLim$. It is recognized that the RstLim ranges from about 1 ohm to about 750 ohms. If no drop in impedance or deviation has occurred then the sealing process was successful and the algorithm proceeds to step 334 as discussed above. If a deviation has been detected, then in step 346 the algorithm performs a subsequent verification.

In step 346, at the onset of successfully meeting both of these conditions, the algorithm begins a timer, DZDT_ZTRAJ_RST_TMR, to define if the deviation event is true and stable or false and transient. In step 348, the algorithm determines whether the measured impedance is above the sum of the reset threshold value, RstLim, the lowest impedance reached, ZLow and the hysteresis value, ZHist. If this condition is satisfied before the timer DZDT_ZTRAJ_RST_TMR expires in step 350, the event is considered transient and the algorithm continues to direct the electrosurgical energy to cause the tissue impedance to follow the previous trajectory by returning to step 332.

If the condition described above in step 348 occurs and the timer expires in step 350, the event is deemed real and the algorithm proceeds to step 352 where the algorithm adjusts to look for tissue reaction as described earlier with respect 318. Specifically, in step 354, the impedance is monitored to identify a rise above the minimum value, Zlow, and once this occurs as represented by phase VII in FIG. 5, the trajectory is recalculated to begin at the new reaction impedance and the trajectory time is reset by returning to step 332 as represented by phase VIII in FIG. 5. The algorithm then continues with the same series of events described previously until tissue fusion is identified. If a rise in impedance is not detected in step 354 within a predetermined period of time then the algorithm proceeds to step 308 and the process ends with a regrasp.

In normal operation, the algorithm directs the RF energy to maintain a match between the tissue impedance and the target value throughout time. Independent of the actual tissue impedance the target trajectory is incremented in a normal fashion during all events unless a reset trajectory is requested. However, the trajectory may enter a holding pattern with respect to the last value at any event when the actual tissue impedance deviates significantly from the target impedance until either a reset condition is requested or the tissue impedance realigns with the target value.

It is recognized that a number of methods not described here are possible to identify the conditions described. The logic intent is to identify an event that results in notable and significant deviation from the impedance target by the tissue and thereby justifying a new target trajectory. Initializing a new trajectory results in mitigating excessive energy delivery to the tissue as the impedance deviates from the target and therefore prevents an uncontrollable tissue effect once the tissue re-reacts.

If during the initial RF energy ramp or during a negative deviation of tissue impedance from the target impedance, the tissue does not rise above the lowest measured impedance by a pre-defined amount within a pre-defined time then the algorithm exits with an alarm. This alerts the user to a possible attempt to seal tissue which is already desiccated or sealed, an attempt to seal tissue which is so large that the tissue is not sufficiently affected by the RF energy delivered, an attempt to seal non-tissue, or a persistent short circuit during the sealing process.

The algorithm according to the present disclosure allows for the slow desiccation of tissue and for collagen to denature in a slow controllable fashion. As desiccation progresses, the resulting seal gains plastic-like qualities, becoming hard and clear, which makes the seal capable of withstanding higher burst pressures.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system comprising:
an electrosurgical forceps including first and second jaw members pivotally attached in opposing relation relative to one another, the jaw members relatively movable from a first, open position wherein the jaw members are disposed in spaced relation relative to one another to a second, clamping position wherein the jaw members cooperate to grasp tissue therebetween with a predetermined clamping force, each of the jaw members including an electrically conductive sealing surface; and
an electrosurgical generator configured to operatively couple to the electrosurgical forceps and to supply electrosurgical energy to the electrically conductive sealing surfaces, the electrosurgical generator including:
at least one input control configured to record a user-defined setting associated with the electrosurgical energy;
at least one sensor configured to measure at least one electrical tissue parameter or at least one electrosurgical energy parameter; and
a controller configured to predict a tissue mass of the tissue grasped by the jaw members based on the at least one electrical tissue parameter or at least one electrosurgical energy parameter and to adjust the user-defined setting as a function of the predicted tissue mass.

2. The electrosurgical system according to claim 1, wherein the controller is configured to predict the tissue mass based on the at least one electrical tissue parameter or the at least one electrosurgical energy parameter measured prior to application of therapeutic energy to the tissue.

3. The electrosurgical system according to claim 2, wherein the controller is further configured to predict the tissue mass based on total energy delivered to tissue prior to application of therapeutic energy to the tissue.

4. The electrosurgical system according to claim 2, wherein the controller is further configured to predict the tissue mass based on a rate of change of impedance of the tissue prior to application of therapeutic energy to the tissue.

5. The electrosurgical system according to claim 1, wherein the user-defined setting is an intensity setting associated with a voltage, current or power curve of the electrosurgical generator.

6. The electrosurgical system according to claim 1, wherein the at least one electrical tissue parameter is tissue impedance and the controller is further configured to determine whether a tissue reaction has occurred as a function of a minimum impedance value and a predetermined rise in impedance, wherein tissue reaction corresponds to a boiling point of tissue fluid.

7. The electrosurgical system according to claim 6, wherein the controller is configured to generate a target impedance trajectory including a plurality of target impedance values as a function of a measured impedance and desired rate of change based on the tissue reaction determination.

8. An electrosurgical system according to claim 7, wherein the controller is configured to drive tissue impedance along the target impedance trajectory by adjusting the output level of the electrosurgical generator to substantially match tissue impedance to a corresponding target impedance value.

9. An electrosurgical system comprising:
an electrosurgical forceps including first and second jaw members pivotally attached in opposing relation relative to one another, the jaw members relatively movable from a first, open position wherein the jaw members are disposed in spaced relation relative to one another to a second, clamping position wherein the jaw members cooperate to grasp tissue therebetween with a predetermined clamping force, each of the jaw members including an electrically conductive sealing surface; and
an electrosurgical generator configured to operatively couple to the electrosurgical forceps and to supply electrosurgical energy to the electrically conductive sealing surfaces, the electrosurgical generator including:
at least one input control configured to record a user-defined setting associated with the electrosurgical energy;
at least one sensor configured to measure at least one electrosurgical energy parameter suitable for determining total energy delivered to tissue; and
a controller configured to predict a tissue mass of the tissue grasped by the jaw members based on the total energy delivered to tissue prior to application of therapeutic energy to the tissue and to adjust the user-defined setting as a function of the predicted tissue mass.

10. The electrosurgical system according to claim 9, wherein the user-defined setting is an intensity setting associated with a voltage, current or power curve of the electrosurgical generator.

11. The electrosurgical system according to claim 9, wherein the at least one electrical tissue parameter is tissue impedance and the controller is further configured to determine whether a tissue reaction has occurred as a function of a minimum impedance value and a predetermined rise in impedance, wherein tissue reaction corresponds to a boiling point of tissue fluid.

12. The electrosurgical system according to claim 11, wherein the controller is configured to generate a target impedance trajectory including a plurality of target impedance values as a function of measured impedance and desired rate of change based on the tissue reaction determination.

13. An electrosurgical system according to claim 12, wherein the controller is configured to drive the tissue impedance along the target impedance trajectory by adjusting the output level of the electrosurgical generator to substantially match the tissue impedance to a corresponding target impedance value.

14. A method for performing an electrosurgical procedure, comprising:
grasping tissue with an electrosurgical forceps, the electrosurgical forceps adapted to connect to an electrosurgical energy source configured to supply electrosurgical energy thereto, the electrosurgical forceps including first and second jaw members pivotally attached in opposing relation relative to one another, the jaw members relatively movable from a first, open position wherein the jaw members are disposed in spaced relation relative to one another to a second, clamping position wherein the jaw members cooperate to grasp tissue therebetween with a predetermined clamping force, each of the jaw members including an electrically conductive sealing surface;
recording a user-defined setting associated with the electrosurgical energy;
supplying the electrosurgical energy to the electrically conductive sealing surfaces;
measuring at least one electrical tissue parameter or at least one electrosurgical energy parameter;
predicting a tissue mass of the tissue grasped by the jaw members based on the at least one electrical tissue parameter or at least one electrosurgical energy parameter; and
adjusting the user-defined setting as a function of the predicted tissue mass.

15. The method according to claim 14, wherein the predicting the tissue mass is performed prior to application of therapeutic energy to the tissue.

16. The method according to claim 14, wherein the predicting the tissue mass further includes determining total energy delivered to tissue prior to application of therapeutic energy to the tissue.

17. The method according to claim 14, wherein the predicting the tissue mass further includes determining a rate of change of impedance of the tissue prior to application of therapeutic energy to the tissue.

18. The method according to claim 14, wherein the user-defined setting is an intensity setting associated with a voltage, current or power curve of the electro surgical generator.

19. The method according to claim 14, comprising:
determining whether tissue reaction has occurred as a function of a minimum impedance value and a predetermined rise in impedance, wherein tissue reaction corresponds to a boiling point of tissue fluid; and
generating a target impedance trajectory as a function of measured impedance and desired rate of change based on the tissue reaction determination, the target impedance trajectory including a plurality of target impedance values.

20. A method according to claim 19, further comprising the step of
driving tissue impedance along the target impedance trajectory by adjusting the output level to substantially match tissue impedance to a corresponding target impedance value.

* * * * *